United States Patent [19]
Burmer et al.

[11] Patent Number: 5,935,788
[45] Date of Patent: Aug. 10, 1999

[54] SUBTRACTIVE HYBRIDIZATION TECHNIQUES FOR IDENTIFYING DIFFERENTIALLY EXPRESSED AND COMMONLY EXPRESSED NUCLEIC ACID

[75] Inventors: Glenna C. Burmer; Joseph P. Brown; Christine C. Stewart, all of Seattle, Wash.

[73] Assignee: Lifespan Biosciences, Inc., Seattle, Wash.

[21] Appl. No.: 08/901,224

[22] Filed: Jul. 24, 1997

Related U.S. Application Data

[60] Provisional application No. 60/022,807, Jul. 25, 1996.
[51] Int. Cl.$^6$ ............................. C12Q 1/68; C12P 19/34; C07H 21/04
[52] U.S. Cl. ......................... 435/6; 435/91.2; 536/23.1; 536/24.2; 536/24.33
[58] Field of Search ..................... 435/6, 91.2; 536/23.1, 536/24.2, 24.33, 24.3

[56] References Cited

U.S. PATENT DOCUMENTS

| | | | |
|---|---|---|---|
| 5,436,142 | 7/1995 | Wigler et al. | 435/91.2 |
| 5,501,964 | 3/1996 | Wigler et al. | 435/91.2 |
| 5,726,022 | 3/1998 | Burmer | 435/6 |

FOREIGN PATENT DOCUMENTS

WO 89/12695  12/1989  WIPO.

OTHER PUBLICATIONS

Yang et al. Cloning differentially expressed genes by linker capture subtraction. Analytical Biochemistry. vol. 237: 109–114. May 21, 1996.

Velculescu et al. Serial analysis of gene expression. Science. vol. 270: 484–487. Oct. 20, 1995.

Lisitsyn, N., et al., "Cloning the Differences Between Two Complex Genomes," Science, vol. 259 (Feb. 12, 1993), pp. 946–951.

*Primary Examiner*—James Ketter
*Assistant Examiner*—William Sandals
*Attorney, Agent, or Firm*—Townsend & Townsend & Crew LLP

[57] ABSTRACT

The present invention provides gene subtraction methods that can be used to identify and isolate from hybridization mixtures differentially expressed nucleic acid and/or commonly expressed nucleic acid between two populations of nucleic acid. The methods of the present invention employ a restriction endonuclease recognition site that is also recognized in whole or in part by a second restriction endonuclease (e.g., HinPI and BssHII or HhaI and HinP1I) to create different ends (e.g., sticky ends) between the first and second nucleic acid populations. In addition, the methods of the present invention use a selective ligation step, a biotinylated nucleotide extension step, or both to differentiate between homoduplexes, which allow for the identification of sequences that are different between the two nucleic acid populations, and heteroduplexes, which allow for the identification of sequences that are common to the two nucleic acid populations.

55 Claims, No Drawings

5,935,788

SEQUENCE LISTING (1) GENERAL INFORMATION:

(iii) NUMBER OF SEQUENCES: 10

(2) INFORMATION FOR SEQ ID NO:1:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:1:

TTTTGCGCNN NNGCGCAAAA

20

(2) INFORMATION FOR SEQ ID NO:2:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:2:

ATATGCGCNN NNGCGCATAT

20

(2) INFORMATION FOR SEQ ID NO:3:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:3:

TTAACGCNNN NGTTAA

16

(2) INFORMATION FOR SEQ ID NO:4:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:4:

TTAACNNNNG CGTTAA

16

(2) INFORMATION FOR SEQ ID NO:5:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:5:

AAAAGGCGCC NNNNGGCGCC TTTT

24

(2) INFORMATION FOR SEQ ID NO:6:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:6:

GCGCCNNNNG

10

(2) INFORMATION FOR SEQ ID NO:7:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:7:

GCCNNNNGGC

10

(2) INFORMATION FOR SEQ ID NO:8:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:8:

TATAGCGCCN NNNGGCGCTA TA

22

(2) INFORMATION FOR SEQ ID NO:9:

(i) SEQUENCE CHARACTERISTICS:
            (A) LENGTH: 20 base
pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:9:

TTAAGCGCCN NNNGGCTTAA

20

(2) INFORMATION FOR SEQ ID NO:10:

(i) SEQUENCE CHARACTERISTICS:
            (A) LENGTH: 20 base
pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:10:

TTAAGCCNNN NGGCGCTTAA

20

SUBTRACTIVE HYBRIDIZATION TECHNIQUES FOR IDENTIFYING DIFFERENTIALLY EXPRESSED AND COMMONLY EXPRESSED NUCLEIC ACID

This application claims the benefit of U.S. Provisional Application No. 60/60/022,807, filed Jul. 25, 1996, the disclosure of which is incorporated by reference.

FIELD OF THE INVENTION

The present invention relates generally to the field of nucleic acid analysis and differentiation. More particularly, the present invention relates to methods which can readily be used to identify from hybridization mixtures, preferably a single hybridization mixture, differentially expressed nucleic acid and/or commonly expressed nucleic acid between two populations of nucleic acid.

BACKGROUND OF THE INVENTION

The ability to identify and target nucleic acid sequences that are differentially expressed and/or commonly expressed between two nucleic acid populations is of intense interest in the field of molecular biology. The identification of such differentially expressed and/or commonly expressed nucleic acid sequences can provide valuable clues as to the genetic bases for disease, inherited dominant and recessive traits, genetic alterations which give rise to diseases such as cancer, species similarities and differences, genotyping and taxonomic classification. As such, this technology has a wide range of applications in diagnostics, medicine, forensics, taxonomic classifications, and the like.

Various comparative nucleic acid techniques are available to analyze differences in nucleic acid populations. One widely known technique is referred to as "representational difference analysis" (RDA); see, for example, U.S. Pat. No. 5,436,142 and Lisitsyn, et al., *Science*, 259:946 (1993). RDA is a subtractive hybridization method that uses restriction digestion of genomic DNA, followed by amplification and selection methods to isolate molecules that are present in one nucleic acid population, but not in a second nucleic acid population. This method, however, requires multiple steps, numerous costly reagents and several weeks of time in the laboratory to obtain results.

Genomic analysis, particularly at the human level, is highly complex and involves the analysis of large amounts of nucleic acid. Processes which can selectively, simply and quickly isolate disease-associated sequences from complex nucleic acid samples will enable the science of molecular biology to uncover keys to the genome and, in turn, to identify the causative agents of various diseases.

SUMMARY OF THE INVENTION

The present invention provides gene subtraction methods that can be used to identify and isolate from hybridization mixtures differentially expressed nucleic acid and/or commonly expressed nucleic acid between two populations of nucleic acid. The methods of the present invention employ a restriction endonuclease recognition site that is also recognized in whole or in part by a second restriction endonuclease (e.g., HinPI and BssHII or HhaI and HinP1I) to create different ends (e.g., sticky ends) between the first and second nucleic acid populations. In addition, the methods of the present invention use a selective ligation step, a biotinylated nucleotide extension step, or both to differentiate between homoduplexes, which allow for the identification of sequences that are different between the two nucleic acid populations, and heteroduplexes, which allow for the identification of sequences that are common to the two nucleic acid populations.

Generally, the methods of the present invention provide for the following: separately fragmenting two populations of nucleic acid, preferably cDNAs, with a sample fragmenting restriction endonuclease to create first and second nucleic acid sample fragments; ligating appropriate adaptors onto the first and second nucleic acid sample fragments and amplifying such fragments using, for example, PCR; fragmenting the first nucleic acid sample fragments with a first restriction endonuclease and the second nucleic acid sample fragments with a second restriction endonuclease; combining the first and second nucleic acid sample fragments under hybridization conditions to form a hybridization mixture; isolating the desired population of target nucleic acid by ligating new adaptors onto desired population, or by extension with a biotinylated nucleotide; and amplifying the captured or non-captured target nucleic acid.

The methods of the present invention are applicable to a wide variety of situations. In determining the presence or absence of particular nucleic acid sequences, particularly associated with recessive or dominant traits, one can compare two related sources of nucleic acid to determine whether they share a particular sequence, where the sequence may be a coding or non-coding sequence, but will be inherited in association with the nucleic acid sequence associated with the trait. One can use the subject methods in forensic medicine, to establish similarities or differences between the nucleic acid from two sources, where one is interested in the degree of relationship between the two sources. The subject methods can also be applied in the study of diseases, where one can investigate the presence of a sequence associated with infection or cause, such as a viral sequence which may or may not be integrated into the genome. Further, similarities and differences can be elucidated in species of interest to aid in taxonomic classification, or to determine possible contamination in nucleic acid samples of interest. Thus, the methods of the present invention have application for detecting genetic rearrangements, for identification of nucleic acid from pathogenic organisms integrated into the genome or present in the cellular source, for identification of polymorphisms located at or near genes associated with inherited disorders, and the like.

Moreover, the methods of the present invention have a number of advantages over RDA. First, in contrast to RDA which uses the selective amplification step to isolate the homodimer tester molecules, the methods of the present invention use a selective ligation step or a selective nucleotide extension step, followed by physical capture. Second, in contrast to RDA which requires the use of different adaptors to regenerate the desired population, the methods of the present invention allow for the same adaptors to be ligated on each time. Three, in contrast to RDA which only identifies differences between the two nucleic acid populations, the methods of the present invention can be used to identify differentially expressed and/or commonly expressed nucleic acid sequences between two nucleic acid populations from the same hybridization mixture. This ability greatly increases the utility of the methods of the present invention. For instance, the recovery of heteroduplexes allows for the identification of sequences that are common to two nucleic acid populations and can be used, after subtraction, to identify sequences that are consistently over- or underexpressed (e.g., for finding a common cancer gene among different types of cancers). Four, in contrast to RDA, the methods of the present invention do not require a single stranded nuclease digestion step. Moreover, the methods of the present invention are much simpler and faster than RDA, and experiments can be performed in a few days rather than several weeks, resulting in savings in both cost and time.

Other features, objects and advantages of the invention and its preferred embodiments will become apparent from the detailed description which follows.

DETAILED DESCRIPTION OF THE INVENTION AND PREFERRED EMBODIMENTS

The present invention provides regenerable gene subtraction methods that can be used to identify and isolate from hybridization mixtures, preferably the same hybridization mixture, differentially expressed nucleic acid and/or commonly expressed nucleic acid between two populations of nucleic acid. As such, the methods and kits of the present invention provide for simple and relatively inexpensive means to determine similarities or differences between two nucleic acid populations. Basically, the methods provide for:

A. Fragmentation of Sample Nucleic Acid Using a Sample Fragmenting Restriction Endonuclease The first nucleic acid sample and the second nucleic acid sample are separately fragmented by using a sample fragmenting restriction endonuclease to create first nucleic acid sample fragments and second nucleic acid sample fragments, respectively. In a presently preferred embodiment, the nucleic acid samples are cDNA samples derived from RNA.

B. Ligation of Adaptors

A pair of first nucleic acid adaptors are ligated onto the first nucleic acid sample fragments, each adaptor having a first restriction endonuclease recognition site that is cleaved by a first restriction endonuclease. Similarly, a pair of second nucleic acid adaptors are ligated onto the second nucleic acid sample fragments, each adaptor having a second restriction endonuclease recognition site which is cleaved by a second restriction endonuclease that recognizes all or a part of the first restriction endonuclease recognition site, but cleaves so that different ends (e.g., sticky ends) are created between the first nucleic acid sample fragments and the second nucleic acid sample fragments. In a presently preferred embodiment, the sample fragmenting restriction endonuclease is the same as the first restriction endonuclease and, thus, they have identical restriction endonuclease recognition sites. In another presently preferred embodiment, the sample fragmenting restriction endonuclease is the same as the second restriction endonuclease and, thus, they have identical restriction endonuclease recognition sites.

C. Fragment Amplification

Once the appropriate adaptors have been ligated onto the first and second nucleic acid sample fragments, the fragments are amplified using primers having a sequence complementary to a sequence of the adaptors. More particularly, the first nucleic acid sample fragments are amplified using a primer having a sequence that is complementary to a sequence of the first nucleic acid adaptors, and the second nucleic acid sample fragments are amplified using a primer having a sequence that is complementary to a sequence of the second nucleic acid adaptors.

D. Fragmentation of First and Second Nucleic Acid Fragments

Once amplified, the first nucleic acid sample is fragmented using the first restriction endonuclease, and the second nucleic acid sample is fragmented using the second restriction endonuclease. Again, the second restriction endonuclease recognizes all or a part of the first restriction endonuclease recognition site, but cleaves so that different ends (e.g., sticky ends) are created between the first and second nucleic acid sample fragments.

E. Hybridization of First and Second Nucleic Acid Fragments

The first and second nucleic acid sample fragments are combined under hybridization conditions to form a hybridization mixture.

F. Isolation of Target Nucleic Acid

The desired target nucleic acid sequence can be isolated from the hybridization mixture by ligating a pair of adaptors onto the target nucleic acid of interest, by using a biotinylated nucleotide or by both ligating a pair of adaptors onto the target nucleic acid of interest and using a biotinylated nucleotide.

It will readily be appreciated by those of skill in the art that if sufficient amounts of nucleic acid are available from the first and second nucleic acid populations, then the ligation and subsequent amplification steps need not be carried out. In this instance, once isolated, the first and second nucleic acid samples would be fragmented using a first restriction endonuclease and a second restriction endonuclease, respectively.

Each of the foregoing steps will be described in greater detail hereinbelow.

A. Fragmentation of Sample Nucleic Acid Using a Sample Fragmenting Restriction Endonuclease For purposes of the present invention, the first and second nucleic acid populations to be analyzed are derived from two or more sources of nucleic acid. The nucleic acid can be from any source in which one is interested in identifying differentially expressed nucleic acid and/or commonly expressed nucleic acid between two nucleic acid populations. Sources of nucleic acid suitable for use in the methods of the present invention include, but are not limited to, eukaryotic or prokaryotic, invertebrate or vertebrate, mammalian or non-mammalian and plant or other higher eukaryotic sources.

The methods of the present invention are particularly well-suited for the use of cDNA. This is especially true when complex genomes are of interest because the use of RNA provides a unique source as it represents an initial simplification of the genome. In addition, it is desirable to use cDNA as the first nucleic acid sample in assays in which cDNA or RNA is used as the second nucleic acid sample so that the isolation of products that are derived from intronic genomic sequences is prevented. For any of the methods described herein, it will be understood that RNA viruses, novel mRNAs expressed in cancers and other RNAs of interest, such as RNA used as a representation of a genome of interest, can be detected by first obtaining the corresponding cDNA. To prepare cDNA, RNA is isolated as a subset of the genomic nucleic acid using any of the isolation methods known in the art and, thereafter, cDNA is synthesized using any of the cDNA synthesis methods known in the art, such as by using reverse transcriptase. See, for example, Innis, et al., *PCR Protocols, infra*, and Ehrlich, ed., *PCR Technology*, W. H. Freeman and Company, N.Y. (1991), the teachings of which are incorporated herein by reference for all purposes.

If genomic DNA is to be the source of the nucleic acid, the DNA is isolated, freed of protein, and then substantially completely digested with a sample fragmenting restriction endonuclease. However, as noted above, RNA is the preferred source of nucleic acid, and cDNA is synthesized from the corresponding RNA, representing a subset of a genomic sample. Normally, the first and second nucleic acid samples will be those which are expected to have substantially similar nucleic acid sequences.

Regardless of the sources of nucleic acid, the first and second nucleic acid samples are separately fragmented using a sample fragmenting restriction endonuclease to create first nucleic acid sample fragments and second nucleic acid sample fragments, respectively. The sample fragmenting restriction endonuclease cuts at the same site that subsequent manipulations are carried out at (e.g., the subsequent ligation of adaptors). Moreover, the sample fragmenting restriction endonuclease provides for staggered (i.e., sticky) ends. It is preferred that both the first and second nucleic acid samples are fragmented using the same sample fragmenting restriction endonuclease, and that the sample fragmenting restriction endonuclease is one which recognizes and cuts at a four base site, leaving an overhang.

Moreover, the sample fragmenting restriction endonuclease, the first restriction endonuclease and the second restriction endonuclease are related and, thus, each is selected with the other two in mind. In a preferred embodiment, the sample fragmenting restriction endonuclease is the same as the first restriction endonuclease and, thus, they have identical restriction endonuclease recognition sites and points of cleavage. Alternatively, the first restriction endonuclease can be different from the sample fragmenting restriction endonuclease. In this embodiment, the first restriction endonuclease is selected so that it recognizes all or a part of the sample fragmenting restriction endonuclease recognition site, but cleaves at a different point. In addition, the second restriction endonuclease is selected so that it recognizes all or a part of the first restriction endonuclease recognition site, but cleaves so that different ends (e.g., sticky ends) are created between the first nucleic acid sample fragments and the second nucleic acid sample fragments.

Preferably, the combination of restriction endonucleases used in the methods of the present invention have the following characteristics: 1) the sample fragmenting restriction endonuclease, e.g., the four base pair restriction enzyme, initially used for cutting the first and second nucleic acid samples, preferably cDNAs, leaves an overhang for ease of subsequent ligation; 2) the restriction sequences that are adapted onto the initial four cutter site do not have as part of their recognition sequences nucleotides that extend into the nucleic acid molecule, e.g., cDNA molecule; and 3) preferably, the restriction sequences that are subsequently adapted onto the initial four cutter site retain the original four cutter site after ligation. Using the following characteristics, those of skill in the art will be able to generate or design different combinations of restriction endonucleases which are suitable for use in the methods of the present invention.

For instance, in a preferred embodiment, the sample fragmenting restriction endonuclease and the first restriction endonuclease are both HinP1I (G'CGC), and the second restriction endonuclease is HhaI (GCG'C). In another preferred embodiment, the sample fragmenting restriction endonuclease and the first restriction endonuclease are both HinP1I (G'CGC), and the second restriction endonuclease is BssHII (G'CGCGC). In another preferred embodiment, the sample fragmenting restriction endonuclease and the first restriction endonuclease are both HinP1I (G'CGC), and the second restriction endonuclease is CfoI (GCG'C). In another preferred embodiment, the sample fragmenting restriction endonuclease and the first restriction endonuclease are both Csp6I (G'TAC), and the second restriction endonuclease is RsaI (GT'AC). In another preferred embodiment, the sample fragmenting restriction endonuclease and the first restriction endonuclease are both MseI (T'TAA), and the second restriction endonuclease is PacI (TTAAT'TAA). In another preferred embodiment, the sample fragmenting restriction endonuclease and the first restriction endonuclease are both AciI (C'GCG), and the second restriction endonuclease is BsrBI (CCG'CTC). In another preferred embodiment, the sample fragmenting restriction endonuclease and the first restriction endonuclease are both AciI (C'GCG), and the second restriction endonuclease is SacII (CCGC'GG). In another preferred embodiment, the sample fragmenting restriction endonuclease and the first restriction endonuclease are both KasI (G'GCGCC), and the second restriction endonuclease is EheI (GGC'GCC). In another preferred embodiment, the sample fragmenting restriction endonuclease and the first restriction endonuclease are both Acc65I (G'GTACC), and the second restriction endonuclease is KpnI (GGTAC'C). In another preferred embodiment, the sample fragmenting restriction endonuclease and the first restriction endonuclease are both ApaI (GGGCC'C), and the second restriction endonuclease is Bsp1201I (G'GGCCC). In another preferred embodiment, the sample fragmenting restriction endonuclease and the first restriction endonuclease are both Ppu10I (A'TGCAT), and the second restriction endonuclease is NsiI (ATGCA'T). In another preferred embodiment, the sample fragmenting restriction endonuclease and the first restriction endonuclease are both SmaI (CCC'GGG), and the second restriction endonuclease is XmaI (C'CCGGG). In another preferred embodiment, the sample fragmenting restriction endonuclease is HaeIII (GG'CC), the first restriction endonuclease is KasI (G'GCGCC) and the second restriction endonuclease is EheI (GGC'GCC).

The foregoing combinations of restriction endonucleases are intended to be illustrative and not restrictive. Almost 1500 restriction endonucleases are now known in the art and at least 150 are commercially available. In addition, complete lists of restriction endonucleases plus details of restriction sites and reaction conditions suitable for their use are published, for example, in Brown, T. A., *Molecular Biology Labfax*, BIOS, Oxford (1991), the teachings of which are incorporated herein by reference. Using this information in combination with the above teachings and examples, those of skill in the art will readily be able to design and generate a multitude of other combinations of restriction endonucleases that are suitable for use in the methods of the present invention.

B. Ligation of Adaptors

Once the first and second nucleic acid samples have been separately fragmented to produce first and second nucleic acid sample fragments, pairs of first and second nucleic acid adaptors are ligated onto the first and second nucleic acid sample fragments, respectively. More particularly, a pair of first nucleic acid adaptors is ligated onto the first nucleic acid sample fragments, each adaptor having a first restriction endonuclease recognition site that is cleaved by a first restriction endonuclease. Similarly, a pair of second nucleic acid adaptors is ligated onto the second nucleic acid sample fragments, each adaptor having a second restriction endonuclease recognition site which is cleaved by a second restriction endonuclease that recognizes all or a part of the first restriction endonuclease recognition site, but cleaves so that different ends (e.g., sticky ends) are created between the first nucleic acid sample fragments and the second nucleic acid sample fragments. Any convenient method for ligation of the adaptors onto the ends of the first and second nucleic acid sample fragments can be employed. Such ligation methods are known to and used by those of skill in the art.

The adaptors used in the methods of the present invention are double-stranded oligonucleotides and will usually be staggered at both ends, with one strand being longer than the other. The adaptors will serve to provide a sequence complementary to a primer to be used if the fragments are amplified in a subsequent amplification step. Moreover, the adaptors will serve to provide a sequence complementary to the ends of the double-stranded nucleic acid sample fragments that result from the fragmentation of the nucleic acid samples using the sample fragmenting restriction endonuclease, sometimes referred to herein as the proximal end of the adaptor. In addition, included within the proximal end of the adaptor is a sequence which incorporates the restriction endonuclease recognition sites that are recognized and cleaved by the first and second restriction endonucleases. As noted above, such restriction endonuclease recognition sites preferably include all or a part of the restriction endonuclease recognition site that is recognized and cleaved by the sample fragmenting restriction endonuclease. Further, it is possible to ligate the same adaptors onto the first and nucleic acid sample fragments if the first and second restriction endonucleases recognize the same restriction endonuclease recognition site, but cleave so that different ends (e.g., sticky ends) are created between the first and second nucleic acid sample fragments.

C. Amplification of First and Second Nucleic Acid Sample Fragments

Once the appropriate adaptors have been ligated onto the first and second nucleic acid sample fragments, the fragments are amplified using primers having a sequence complementary to a sequence of the adaptors. More particularly, the first nucleic acid sample fragments are amplified using a primer having a sequence that is complementary to a sequence of the first nucleic acid adaptors and, similarly, the second nucleic acid sample fragments are amplified using a primer having a sequence that is complementary to a sequence of the second nucleic acid adaptors.

Preferably, the first and second nucleic acid sample fragments are amplified using the polymerase chain reaction (PCR) or, alternatively, using other amplification techniques known to and used by those of skill in the art and discussed in general hereinbelow. In a presently preferred embodiment, the first and second nucleic acid sample fragments are separately amplified by adding appropriate primers and using PCR, usually employing at least about 10 cycles, more usually at least about 30 cycles and generally not more than about 30 cycles, more usually not more than about 25 cycles and preferably about 20 cycles. The number of cycles employed will vary depending upon the initial concentration of the first and second nucleic acid sample fragments being amplified. For a general overview of PCR, see, e.g., PCR Protocols: A Guide to Methods and Applications (Innis, M.; Gelfand, D.; Sninsky, J. and White, T. (Eds.); Academic Press, San Diego (1990)), and U.S. Pat. Nos. 4,683,195 and 4,683,202, the teachings of which are incorporated herein by reference.

D. Fragmentation of First and Second Nucleic Acid Fragments

Once amplified, the first nucleic acid sample is fragmented using the first restriction endonuclease, and the second nucleic acid sample is fragmented using the second restriction endonuclease. In a presently preferred embodiment, the first restriction endonuclease is the same as the sample fragmenting restriction endonuclease. Moreover, the second restriction endonuclease recognizes all or a part of the first restriction endonuclease recognition site, but cleaves so that different ends (e.g., sticky ends) are created between the first and second nucleic acid sample fragments.

As noted above, in a preferred embodiment, the sample fragmenting restriction endonuclease and the first restriction endonuclease are both HinP1I (G'CGC), and the second restriction endonuclease is HhaI (GCG'C). In another preferred embodiment, the sample fragmenting restriction endonuclease and the first restriction endonuclease are both HinP1I (G'CGC), and the second restriction endonuclease is BssHII (G'CGCGC). In another preferred embodiment, the sample fragmenting restriction endonuclease and the first restriction endonuclease are both HinP1I (G'CGC), and the second restriction endonuclease is CfoI (GCG'C). In another preferred embodiment, the sample fragmenting restriction endonuclease and the first restriction endonuclease are both Csp6I (G'TAC), and the second restriction endonuclease is RsaI (GT'AC). In another preferred embodiment, the sample fragmenting restriction endonuclease and the first restriction endonuclease are both MseI (T'TAA), and the second restriction endonuclease is PacI (TTAAT'TAA). In another preferred embodiment, the sample fragmenting restriction endonuclease and the first restriction endonuclease are both AciI (C'GCG), and the second restriction endonuclease is BsrBI (CCG'CTC). In another preferred embodiment, the sample fragmenting restriction endonuclease and the first restriction endonuclease are both AciI (C'GCG), and the second restriction endonuclease is SacII (CCGC'GG). In another preferred embodiment, the sample fragmenting restriction endonuclease and the first restriction endonuclease are both KasI (G'GCGCC), and the second restriction endonuclease is EheI (GGC'GCC). In another preferred embodiment, the sample fragmenting restriction endonuclease and the first restriction endonuclease are both Acc65I (G'GTACC), and the second restriction endonuclease is KpnI (GGTAC'C). In another preferred embodiment, the sample fragmenting restriction endonuclease and the first restriction endonuclease are both ApaI (GGGCC'C), and the second restriction endonuclease is Bsp120I (G'GGCCC). In another preferred embodiment, the sample fragmenting restriction endonuclease and the first restriction endonuclease are both Ppu10I (A'TGCAT), and the second restriction endonuclease is NsiI (ATGCA'T). In another preferred embodiment, the sample fragmenting restriction endonuclease and the first restriction endonuclease are both SmaI (CCC'GGG), and the second restriction endonuclease is XmaI (C'CCGGG). In another preferred embodiment, the sample fragmenting restriction endonuclease is HaeIII (GG'CC), the first restriction endonuclease is KasI (G'GCGCC) and the second restriction endonuclease is EheI (GGC'GCC).

The foregoing combinations of restriction endonucleases are illustrative and not restrictive. Using the above teachings and examples, those of skill in the art will readily be able to design and generate a multitude of other combinations of restriction endonucleases that are suitable for use in the methods of the present invention.

E. Hybridization of First and Second Nucleic Acid Fragments

The first and second nucleic acid sample fragments are combined under hybridization conditions to form a hybridization mixture. More particularly, the first and second nucleic acid sample fragments are combined under hybridization conditions so that the first and second nucleic acid sample fragments hybridize together creating essentially three different hybridization complexes: first nucleic acid/second nucleic acid matches (first nucleic acid:second nucleic acid heteroduplexes), first nucleic acid/first nucleic acid matches (first nucleic acid:first nucleic acid homoduplexes) and second nucleic acid/second nucleic acid matches (second nucleic acid:second nucleic acid homoduplexes). Typically, if heteroduplexes are to be isolated, the first nucleic acid sample fragments and the second nucleic acid sample fragments are present at a ratio of about 1:1. If homoduplexes are to be isolated, the first nucleic acid sample fragments and the second nucleic acid sample fragments are present at a ratio of 1:5 to about 1:500 and, more preferably, at a ratio of about 1:100. Typically, the hybridization reaction will be carried out at high stringency temperatures, usually at about 60–70° C. In addition, the various buffers and salt concentrations used can be adjusted to achieve the necessary stringency using techniques known to those of skill in the art. Typically, fairly high stringencies will be employed.

F. Isolation of Target Nucleic Acid

As noted above, one of the advantages of the methods of the present invention is that they can be used to identify and isolate from hybridization mixtures differentially expressed nucleic acid and/or commonly expressed nucleic acid between two populations of nucleic acid. Generally, the desired target nucleic acid can be isolated from the hybridization mixture by ligating a pair of adaptors onto the target nucleic acid of interest or, alternatively, by using a biotinylated nucleotide, both of which are followed by physical capture of the desired target nucleic acid using, for example, streptavidin capture. It will be readily apparent to those of skill in the art that in addition to biotin/streptavidin capture, other ligand/anti-ligand capture methods can be employed to isolate the target nucleic acid of interest (see, infra, for other ligand/anti-ligand capture methods which can be employed in the methods of the present invention).

The target nucleic acid of interest, whether it be a homoduplex, a heteroduplex or both a homoduplex and a heteroduplex, can be further amplified and isolated, for example, by ligating new adaptors onto the ends of the target nucleic acid molecules and amplifying such molecules using PCR. In addition, it may be advantageous to carry out the entire subtractive hybridization process more than once. In a preferred embodiment, the entire subtractive hybridization process is carried out for two to three cycles.

As noted above, the methods of the present invention can advantageously be used to isolate from hybridization mixtures homoduplexes, which can be used to identify sequences which differ between the two nucleic acid populations, and/or heteroduplexes, which can be used to identify sequences which are in common between the two nucleic acid populations. Thus, depending on what is isolated, the resulting target nucleic acid can be used as probes to identify sequences which differ between the two nucleic acid populations and/or to identify sequences which are in common between the two nucleic acid populations. When used as probes, the target nucleic acid can be labeled in a variety of ways, such as with radioactive labels, biotin, fluorophores, etc. Desirably, in order to obtain substantially homogeneous compositions of each of the target nucleic acid, the target nucleic acid can be cloned by inserting it into an appropriate cloning vector for cloning in a prokaryotic host. If desired, the cloned nucleic acid can be sequenced to determine the nature of the target nucleic acid. Alternatively, the cloned nucleic acid can be labeled and used as probes to identify fragments in libraries carrying the target nucleic acid. The target nucleic acid can be used to identify the similarities and/or differences which may be present between the two sources of nucleic acid.

Using the methods of the present invention, the resulting target nucleic acid will be greatly enriched. The target nucleic acid may be sequenced directly after PCR or, as noted above, it may be cloned by inserting it in a cloning vector for cloning into a host cell. The cloned DNA can subsequently be sequenced to determine the nature of the target DNA through the use of dot blotting or other procedures. Sequences can be identified and cloned for sequencing. Comparative searches with sequences described in accessible libraries can aid in identifying the sequence. Such libraries include, for example, Genbank (National Center for Biotechnology Information, Natl. Library of Medicine, National Institutes of Health, 8600 Rockville Pike, Bethesda, Md. 20894); and Protein Identification Resource (PIR, Natl. Biomedical Research Foundation, 3900 Reservoir Road NW, Washington, D.C. 20007; EMBL, European Molecular Biology Laboratory, Heidelberg, Germany).

G. Kits

In another aspect, the present invention provides kits for carrying out the methods described herein. Combinations of reagents useful in the methods set out above can be packaged together with instructions for using them in the described methods. In particular, such kits can contain a separate container for the first nucleic acid sample adaptors and for the second nucleic acid sample adaptors. Preferably, such kits will also contain instructions for carrying out the subtractive capture methods described herein. Alternatively, the kits can contain separate containers for primers to amplify the first nucleic acid sample fragments and primers to amplify the second nucleic acid sample fragments as described above. Further, the kits can also contain separate containers of first nucleic acid sample adaptors, second nucleic acid sample adaptors, first nucleic acid sample primers and second nucleic acid sample primers, all as described above. Moreover, the kits can contain a pair of adaptors and/or a biotinylated nucleotide which can be used to isolated the target nucleic acid of interest.

H. Other Definitions and General Techniques

The term "ligand" refers to a component which can directly or indirectly be detected or captured by another component, the "anti-ligand" which permits the physical or chemical separation of compositions bearing the ligand from those which do not. The ligand will be attracted to an anti-ligand molecule such that molecules which do not bear the ligand will not be captured or otherwise attracted to the anti-ligand. The ligand will need to be one which may be attached directly or indirectly to nucleic acid sequences. Examples of direct ligand binding include the use of biotin labeled nucleotides or the use of digoxigenin. Such molecules can be used as the ligand component and can readily be captured by their anti-ligand, e.g., avidin or streptavidin in the case of biotin and an anti-digoxigenin antibody, bound on a suitable substrate. (These reagents are all commercially available from a number of different sources. See, e.g., Clontech Laboratories, Inc. (Palo Alto, Calif.) for digoxigenin reagents.) Molecules which do not bind the anti-ligand can be collected and captured, for example, by passing them through a streptavidin column. This direct capture method is preferred as it is likely to be the simplest, least costly and most efficient of the capture technologies available.

Nevertheless, other methods can be used as well so long as they accomplish a similar purpose. For example, the ligand could be a specific nucleic acid sequence with the anti-ligand being the complement of the sequence, or an antibody specific for the sequence. The ligand could include labeled molecules which may be manipulated on a substrate so that they are physically or chemically separated from non-ligand bearing molecules. Alternatively, the ligand molecule can have an affinity for an anti-ligand molecule which is labeled or inherently detectable. These compositions can be further detected by spectroscopic, photochemical, biochemical, immunochemical or other chemical means. For example, useful nucleic acid labels can include enzymes (e.g., LacZ, CAT, horse radish peroxidase, alkaline phosphatase and others, commonly used as detectable enzymes, either as marker gene products or in an ELISA), nucleic acid intercalators (e.g., ethidium bromide), colorimetric labels such as colloidal gold or colored glass or plastic (e.g., polystyrene, polypropylene, latex, etc.) beads, substrates, cofactors, inhibitors, fluorescent moieties (e.g., fluorescein and its derivatives, Texas red, rhodamine and its derivatives, dansyl, umbelliferone and the like), chemiluminescent moieties (e.g., luciferin and 2,3-dihydrophthalazinediones), magnetic particles, and the like. Labeling agents optionally include, for example, monoclonal antibodies, polyclonal antibodies, proteins and other polymers, such as affinity matrices, carbohydrates or lipids, fluorescent dyes, electron-dense reagents, enzymes (e.g., as commonly used in an ELISA), or haptens and proteins for which antisera or monoclonal antibodies are available. A wide variety of labels suitable for labeling nucleic acids and conjugation techniques for labeling nucleic acids are known and are reported extensively in both the scientific and patent literature, and are generally applicable to the present invention for the labeling of nucleic acids, or amplified nucleic acids for detection and isolation by the methods of the invention. The choice of label depends on the sensitivity required, ease of conjugation of the compound, stability requirements, available instrumentation and disposal provisions. Separation and detection of nucleic acids proceeds by any known method, including immunoblotting, tracking of radioactive or bioluminescent markers, Southern blotting, northern blotting, southwestern blotting, northwestern blotting, or other methods which track a molecule based upon size, charge or affinity.

Means of detecting labels are well known to those of skill in the art. Thus, for example, where the label is a radioactive label, means for detection include a scintillation counter or photographic film as in autoradiography. Where the label is a fluorescent label, it may be detected by exciting the fluorochrome with the appropriate wavelength of light and detecting the resulting fluorescence, e.g., by microscopy, visual inspection, via photographic film, by the use of electronic detectors such as charge coupled devices (CCDs) or photomultipliers and the like.

Similarly, enzymatic labels may be detected by providing appropriate substrates for the enzyme and detecting the resulting reaction product. Finally, simple calorimetric labels are often detected simply by observing the color associated with the label. Thus, in various dipstick assays, conjugated gold often appears pink, while various conjugated beads appear the color of the bead.

Substrates to be used as an environment for the capture and separation of the ligand bound molecules from those without ligand depend on the ligand being used and the desired format. For instance, the solid surface is optionally paper, or a membrane (e.g., nitrocellulose), a microtiter dish (e.g., PVC, polypropylene, or polystyrene), a test tube (glass or plastic), a dipstick (e.g., glass, PVC, polypropylene, polystyrene, latex, and the like), a microcentrifuge tube, or a glass, silica, plastic, metallic or polymer bead or other substrate as described herein. The desired anti-ligand may be covalently bound, or noncovalently attached to the substrate through nonspecific bonding.

A wide variety of organic and inorganic polymers, both natural and synthetic may be employed as the material for the solid surface. Illustrative polymers include polyethylene, polypropylene, poly(4-methylbutene), polystyrene, polymethacrylate, poly(ethylene terephthalate), rayon, nylon, poly(vinyl butyrate), polyvinylidene difluoride (PVDF), silicones, polyformaldehyde, cellulose, cellulose acetate, nitrocellulose, and the like. Other materials which are appropriate depending on the assay include paper, glasses, ceramics, metals, metalloids, semiconductive materials, cements and the like. In addition, substances that form gels, such as proteins (e.g., gelatins), lipopolysaccharides, silicates, agarose and polyacrylamides can be used. Polymers which form several aqueous phases, such as dextrans, polyalkylene glycols or surfactants, such as phospholipids, long chain (12–24 carbon atoms) alkyl ammonium salts and the like are also suitable. Where the solid surface is porous, various pore sizes may be employed depending upon the nature of the system.

In preparing the surface, a plurality of different materials are optionally employed, e.g., as laminates, to obtain various properties. For example, protein coatings, such as gelatin can be used to avoid non specific binding, simplify covalent conjugation, enhance signal detection or the like. If covalent bonding between a compound and the surface is desired, the surface will usually be polyfunctional or be capable of being polyfunctionalized. Functional groups which may be present on the surface and used for linking can include carboxylic acids, aldehydes, amino groups, cyano groups, ethylenic groups, hydroxyl groups, mercapto groups and the like. In addition to covalent bonding, various methods for noncovalently binding an anti-ligand component can be used. For additional information regarding suitable ligand-anti-ligand and labeling technology as it relates to nucleic acids, see, for example, *Essential Molecular Biology*, ed. T. A. Brown IRL Press (1993); *In Situ Hybridization Protocols*, ed. K. H. Andy Choo, Humana Press (1994).

By a nucleic acid sequence "homologous to" or "complementary to", it is meant a nucleic acid that hybridizes, duplexes or binds only to DNA sequences encoding one protein or portions thereof. A DNA sequence which is homologous to a target sequence can include sequences which are shorter or longer than the target sequence so long as they meet the functional test set forth. Hybridization conditions are specified along with the source of the DNA. Typically, the hybridization is done in solution using a 1M NaCl, EPPS buffer, small vol. high conc.–8 $\mu g/\mu l$, 67° C.

Accepted means for conducting hybridization assays are known and general overviews of the technology can be had from a review of: *Nucleic Acid Hybridization: A Practical Approach*, Ed. Hames, B. D. and Higgins, S. J., IRL Press, 1985; *Hybridization of Nucleic Acids Immobilized on Solid Supports*, Meinkoth, J. and Wahl, G.; *Analytical Biochemistry*, 238:267–284, 1984 and Innis, et al., *PCR Protocols*, supra, all of which are incorporated by reference herein.

Nucleic acids of interest in the present invention may be cloned or amplified, or any of the nucleic acid fragments may be amplified by in vitro methods, such as the polymerase chain reaction (PCR), the ligase chain reaction (LCR), the transcription-based amplification system (TAS), the self-sustained sequence replication system (3SR) and the Qβ replicase amplification system (QB). A wide variety of cloning and in vitro amplification methodologies are well-known to persons of skill. Examples of these techniques and instructions sufficient to direct persons of skill through many cloning exercises are found in Berger and Kimmel, *Guide to Molecular Cloning Techniques, Methods in Enzymology* 152 Academic Press, Inc., San Diego, Calif. (Berger); Sambrook, et al. (1989) *Molecular Cloning—A Laboratory*

Manual (2nd ed.) Vol. 1–3, Cold Spring Harbor Laboratory, Cold Spring Harbor Press, N.Y., (Sambrook, et al.); Current Protocols in Molecular Biology, F. M. Ausubel, et al., eds., Current Protocols, a joint venture between Greene Publishing Associates, Inc. and John Wiley & Sons, Inc., (1994 Supplement) (Ausubel); Cashion, et al., U.S. Pat. No. 5,017, 478; and Carr, European Patent No. 0,246,864. Examples of techniques sufficient to direct persons of skill through in vitro amplification methods are found in Berger, Sambrook, and Ausubel, as well as Mullis, et al., (1987) U.S. Pat. No. 4,683,202; PCR Protocols A Guide to Methods and Applications (Innis, et al. eds) Academic Press Inc. San Diego, Calif. (1990) (Innis); Arnheim & Levinson (Oct. 1, 1990) C&EN 36–47; The Journal Of NIH Research (1991) 3:81–94; (Kwoh, et al. (1989) Proc. Natl. Acad. Sci. USA, 86:1173; Guatelli, et al. (1990) Proc. Natl. Acad. Sci. USA, 87:1874; Lomell, et al. (1989) J. Clin. Chem. 35:1826; Landegren, et al., (1988) Science, 241:1077–1080; Van Brunt (1990) Biotechnology, 8:291–294; Wu and Wallace, (1989) Gene, 4:560; and Barringer, et al. (1990) Gene, 89:117.

The term "identical" in the context of two nucleic acid sequences refers to the residues in the two sequences which are the same when aligned for maximum correspondence. Sequences which are not identical are "different."

The invention will be described in greater detail by way of specific examples. The following examples are offered for illustrative purposes, and are not intended to limit the invention in any manner. Those of skill in the art will readily recognize a variety of noncritical parameters which can be changed or modified to yield essentially the same results.

EXAMPLES

A. Example 1

In this example, a combination of restriction enzymes is used which allows for the isolation of either homoduplex A:A or B:B, as well as the heteroduplex A:B. This example uses the same four base pair recognition site (GCGC) to create the initial amplified populations A and B from the cDNAs, but allows one to subsequently differentiate between the two populations by using different restriction enzymes that recognize the same GCGC site, but produce different ends after digestion. Both homoduplex species can be isolated by ligation of adaptors with the appropriate ends, followed by amplification with primers homologous to those adaptors. The heteroduplex has blunt ends and, thus, can be isolated by first biotinylating the homoduplexes (by filling in with biotinylated nucleotides or ligation of sticky-ended biotinylated adaptors) and removing them by biotin capture, followed by ligation of blunt-ended adaptors to the remaining heteroduplex molecules and amplification with primers homologous to the new adaptors.

1. Step 1

Synthesize cDNA from mRNA of population A and population B. This step can use any number of commercially available cDNA synthesis methods, including oligo-dT in the first strand and random hexamers in the second, or random hexamers during both first and second strand synthesis.

2. Step 2

Digest populations A and B with HinP1I (G'CGC), ligate adaptors restoring the complete restriction site, and amplify to create amplicon populations.

3. Step 3

Digest population A with HhaI (GCG'C) and population B with HinP1I (G'CGC), remove adaptors and hybridize. N is a specific gene sequence of A, C, G, or T. Four products are found in the hybridization mixture:

```
5'CNNNNGCG3'    A:A homodimer with 3'CG overhang
3'GCGNNNNC5'

5'CGCNNNNG3'    B:B homodimer with 5'CG overhang
  3'GNNNNCGC5'

5'CGCNNNNG3'    A:B heteroduplex with blunt ends
3'GCGNNNNC5'

5'CNNNNGCG3'    A:B heteroduplex with blunt ends
3'GNNNNCGC5'
```

4. Step 4A

Capture A:A homodimer by ligating nonphosphorylated adaptors with 3'CG overhangs:

| Adaptor 1A | HomodimerA | Adaptor 1A |
|---|---|---|
| 5'TTTTGCG3' | 5'CNNNNGCG3' | 5' CAAAA3' |
| 3'AAAAC5' | 3'GCGNNNNC5' | 3'GCGTTTT5' |

The following is the resulting ligation product:

5'TTTTGCGCNNNNGCGCAAAA3' (SEQ ID NO:1)

3'AAAACGCGNNNNCGCGTTTT5' (SEQ ID NO:1)

Step 4B

Capture B:B homodimer by either a) incorporating biotinylated dC into an extension reaction with a polymerase lacking 3'-5' exonuclease (such as Klenow 3'-5' exo-), followed by capture with streptavidin or b) ligating nonphosphorylated adaptors with a 5'CG overhang:

| Adaptor 1B | Homodimer B | Adaptor 1B |
|---|---|---|
| 5' ATATG3' | 5'CGCNNNNG3' | 5'CGCATAT3' |
| 3' TATACGC5' | 3'GNNNNCGC5' | 3'GTATA5' |

The following is the resulting ligation product:

5'ATATGCGCNNNNGCGCATAT3' (SEQ ID NO:2)

3'TATACGCGNNNNCGCGTATA5' (SEQ ID NO:2)

Step 4C

Capture A:B heterodimer by first removing the homodimers by biotin capture after ligation of the appropriate biotinylated adaptors. Then, ligate nonphosphorylated blunt-ended adaptors:

| Adaptor 1C | Heterodimers | Adaptor 1C |
|---|---|---|
| 5'TTAA3' | 5'CGCNNNNG3' or 5'CNNNNGCG3' | 5'TTAA3' |
| 3'AATT5' | 3'GCGNNNNC5' or 3'gNNNNCGC5' | 3'AATT5' |

The following is the resulting ligation product:

5'TTAACGCNNNNGTTAA3' (SEQ ID NO:3) or 5'TTAACNNNNGCGTTAA3' (SEQ ID NO:4)

3'AATTGCGNNNNCAATT5' (SEQ ID NO:3) or 3'AATTGNNNNCGCAATT5' (SEQ ID NO:3)

5. Step 5

Melt away nonphosphorylated adaptor and fill in ends with polymerase then amplify with adaptor set 1A for A:A homodimer, adaptor set 1B for B:B homodimer, or adaptor set 1C for A:B heterodimer.

B. Example 2

In this example, amplicons are produced from cDNA by using a restriction enzyme recognizing a four base pair restriction site (GGCC) to create blunt ends, then ligating blunt-ended adaptors which create a six base pair restriction site (GGCGCC). The latter site can be digested by different enzymes, leaving either blunt ends or four base pair overhangs. Under these conditions, the heteroduplex can be isolated using selective ligation by virtue of its specific (two base pair overhang) ends.

1. Step 1 and 2

Synthesize cDNA from mRNA of population A and population B, cut CDNA with HaeIII (GG'CC) and ligate adaptors creating the restriction site GGCGCC:

| Adaptor 2A | cut cDNA | Adaptor 2A |
|---|---|---|
| 5'AAAAGGCG3' | 5'CCNNNNGG3' | 5'CGCCTTTT3' |
| 3'TTTTCCGC5' | 3'GGNNNNCC5' | 3'GCGGAAAA5' |

The following is the resulting ligation product:

5'AAAAGGCGCCNNNNGGCGCCTTTT3' (SEQ ID NO:5)

3'TTTTCCGCGGNNNNCCGCGGAAAA5' (SEQ ID NO:5)

2. Step 3

Digest population A with KasI (G'GCGCC) and population B with EheI (GGC'GCC), remove adaptors and hybridize. N is a specific gene sequence of A, C, G, or T. Four products are found in the hybridization mixture:

| 5'GCGCCNNNNG3' | (SEQ ID NO:6) | A:A homodimer |
| 3'GNNNNCCGCG5' | (SEQ ID NO:6) | |

-continued

| 5'GCCNNNNGGC3' | (SEQ ID NO:7) | B:B homodimer |
| 3'CGGNNNNCCG5' | (SEQ ID NO:7) | |
| 5'GCGCCNNNNG3' | (SEQ ID NO:6) | A:B heterodimer |
| 3'CGGNNNNCCG5' | (SEQ ID NO:7) | |
| 5'GCCNNNNGGC3' | (SEQ ID NO:7) | A:B heterodimer |
| 3'GNNNNCCGCG5' | (SEQ ID NO:6) | |

3. Step 4A

Capture A:A homodimer by ligating nonphosphorylated four base pair overhang adaptors:

| Adaptor 2B | HomodimerA | | Adaptor 2B |
|---|---|---|---|
| 5'TATA3' | 5'GCGCCNNNNG3' | (SEQ ID NO:6) | 5'GCGCTATA3' |
| 3'ATATCGCG5' | 3'GNNNNCCGCG5' | (SEQ ID NO:6) | 3'ATAT5' |

The following is the resulting ligation product:

5'TATAGCGCCNNNNGGCGCTATA3' (SEQ ID NO:8)

3'ATATCGCGGNNNNCCGCGATAT5' (SEQ ID NO:8)

Step 4B

Capture A:B heterodimer by ligating nonphosphorylated two base pair overhang adaptors:

| Adaptor 2C | | Heterodimers | | Adaptor 2C |
|---|---|---|---|---|
| 5'TTAA3' | 5'GCGCCNNNNG3' | (SEQ ID NO:6) or 5'GCCNNNNGGC3' | (SEQ ID NO:7) | 5'GCTTAA3' |
| 3'AATTCG5' | 3'CGGNNNNCCG5' | (SEQ ID NO:7) or 3'GNNNNCCGCG5' | (SEQ ID NO:6) | 3'AATT5' |

The following are the resulting ligation products:

5'TTAAGCGCCNNNNGGCTTAA3' (SEQ ID NO:9)

3'AATTCGCGGNNNNCCGAATT5' (SEQ ID NO:10)

5'TTAAGCCNNNNGGCGCTTAA3' (SEQ ID NO:10)

3'AATTCGGNNNNCCGCGAATT5' (SEQ ID NO:9)

4. Step 5

Melt away nonphosphorylated adaptor and fill in ends with polymerase then amplify with adaptor set 2B for A:A homodimer or adaptor set 2C for A:B heterodimer.

It is to be understood that the above description is intended to be illustrative and not restrictive. Many embodiments will be apparent to those of skill in the art upon reading the above description. The scope of the invention should, therefore, be determined not with reference to the above description, but should instead be determined with reference to the appended claims, along with the full scope of equivalents to which such claims are entitled. The disclosures of all articles and references, including patent applications and publications, are incorporated herein by reference for all purpose.

What is claimed is:

1. A method for detecting a target nucleic acid present in a first nucleic acid population (a first nucleic acid sample) and not in a second nucleic acid population (a second nucleic acid sample), said method comprising:
    (a) separately fragmenting nucleic acid from said first nucleic acid sample and nucleic acid from said second nucleic acid sample with a sample fragmenting restriction endonuclease to create first nucleic acid sample fragments and second nucleic acid sample fragments, respectively;
    (b) ligating a pair of first nucleic acid adaptors onto said first nucleic acid sample fragments, each adaptor having a first restriction endonuclease recognition site that is cleaved by a first restriction endonuclease, and amplifying said first nucleic acid sample fragments with a primer having a sequence that is complementary to a sequence of said first nucleic acid adaptors;
    (c) ligating a pair of second nucleic acid adaptors onto said second nucleic acid sample fragments, each adaptor having a second restriction endonuclease recognition site which is cleaved by a second restriction endonuclease that recognizes all or a part of said first restriction endonuclease recognition site, but cleaves so that different ends are created between said first nucleic acid sample fragments and said second nucleic acid sample fragments, and amplifying said second nucleic acid sample fragments with a primer having a sequence that is complementary to a sequence of the second nucleic acid adaptors;
    (d) fragmenting said first nucleic acid sample fragments with said first restriction endonuclease and said second nucleic acid sample fragments with said second restriction endonuclease; then
    (e) combining said first nucleic acid sample fragments and said second nucleic acid sample fragments under hybridization conditions to form a hybridization mixture; and
    (f) isolating a homoduplex from said hybridization mixture, wherein the isolation of said homoduplex identifies target nucleic acid which is present in said first nucleic acid sample and not in said second nucleic acid sample.

2. The method in accordance with claim 1, wherein said nucleic acid is cDNA.

3. The method in accordance with claim 1, wherein said nucleic acid is derived from a source selected from the group consisting of eukaryotic, prokaryotic, invertebrate, vertebrate, mammalian, non-mammalian and plant.

4. The method in accordance with claim 1, wherein said sample fragmenting restriction endonuclease and said first restriction endonuclease are the same.

5. The method in accordance with claim 1, wherein said sample fragmenting restriction endonuclease and said first restriction endonuclease are both HinP1I, and said second restriction endonuclease is HhaI.

6. The method in accordance with claim 1, wherein said sample fragmenting restriction endonuclease and said second restriction endonuclease are both HinP1I, and said first restriction endonuclease is HhaI.

7. The method in accordance with claim 1, wherein said sample fragmenting restriction endonuclease is HaeIII, said first restriction endonuclease is KasI, and said second restriction endonuclease is EheI.

8. The method in accordance with claim 1, wherein said homoduplex of step (f) is isolated from said hybridization mixture using a biotinylated nucleotide.

9. The method in accordance with claim 1, wherein said homoduplex of step (f) is isolated from said hybridization mixture by ligating a pair of adaptors onto said homoduplex.

10. The method in accordance with claim 1, wherein said first restriction endonuclease and said second restriction endonuclease, respectively, are selected from the group consisting of:

HinP1I and HhaI;
HinP1I and CfoI;
Csp6I and RsaI;
HinP1I and BssHII;
MseI and PacI;
AciI and BsrBI;
AciI and SacII;
KasI and EheI;
Acc65I and KpnI;
ApaI and Bsp120I;
Ppu10I and NsiI; and
SmaI and XmaI.

11. The method in accordance with claim 10, wherein said sample fragmenting restriction endonuclease and said first restriction endonuclease are the same.

12. A method for detecting a target nucleic acid present in both a first nucleic acid population (a first nucleic acid sample) and a second nucleic acid population (a second nucleic acid sample), said method comprising:

(a) separately fragmenting nucleic acid from said first nucleic acid sample and nucleic acid from said second nucleic acid sample with a sample fragmenting restriction endonuclease to create first nucleic acid sample fragments and second nucleic acid sample fragments, respectively;

(b) ligating a pair of first nucleic acid adaptors onto said first nucleic acid sample fragments, each adaptor having a first restriction endonuclease recognition site that is cleaved by a first restriction endonuclease, and amplifying said first nucleic acid sample fragments with a primer having a sequence that is complementary to a sequence of said first nucleic acid adaptors;

(c) ligating a pair of second nucleic acid adaptors onto said second nucleic acid sample fragments, each adaptor having a second restriction endonuclease recognition site which is cleaved by a second restriction endonuclease that recognizes all or a part of said first restriction endonuclease recognition site, but cleaves so that different ends are created between said first nucleic acid sample fragments and said second nucleic acid sample fragments, and amplifying said second nucleic acid sample fragments with a primer having a sequence that is complementary to a sequence of the second nucleic acid adaptors;

(d) fragmenting said first nucleic acid sample fragments with said first restriction endonuclease and said second nucleic acid sample fragments with said second restriction endonuclease; then (e) combining said first nucleic acid sample fragments and said second nucleic acid sample fragments under hybridization conditions to form a hybridization mixture; and (f) isolating a heteroduplex from said hybridization mixture, wherein the isolation of said heteroduplex identifies second target nucleic acid which is present in both said first nucleic acid sample and said second nucleic acid sample.

13. The method in accordance with claim 12, wherein said nucleic acid is cDNA.

14. The method in accordance with claim 12, wherein said nucleic acid is derived from a source selected from the group consisting of eukaryotic, prokaryotic, invertebrate, vertebrate, mammalian, non-mammalian and plant.

15. The method in accordance with claim 12, wherein said sample fragmenting restriction endonuclease and said first restriction endonuclease are the same.

16. The method in accordance with claim 12, wherein said sample fragmenting restriction endonuclease and said first restriction endonuclease are both HinpI, and said second restriction endonuclease is HhaI.

17. The method in accordance with claim 12, wherein said sample fragmenting restriction endonuclease and said second restriction endonuclease are both HinP1I, and said first restriction endonuclease is HhaI.

18. The method in accordance with claim 12, wherein said sample fragmenting restriction endonuclease is HaeIII, said first restriction endonuclease is KasI, and said second restriction endonuclease is EheI.

19. The method in accordance with claim 12, wherein said heteroduplex of step (g) is isolated from said hybridization mixture using a biotinylated nucleotide.

20. The method in accordance with claim 12, wherein said heteroduplex of step (g) is isolated from said hybridization mixture by ligating a pair of adaptors onto said heteroduplex.

21. The method in accordance with claim 12, wherein said first restriction endonuclease and said second restriction endonuclease, respectively, are selected from the group consisting of:

HinP1I and HhaI;
HinP1I and CfoI;
Csp6I and RsaI;
HinP1I and BssHII;
MseI and PacI;
AciI and BsrBI;
AciI and SacII;
KasI and EheI;
Acc65I and KpnI;
ApaI and Bsp120I;
Ppu10I and NsiI; and
SmaI and XmaI.

22. The method in accordance with claim 21, wherein said sample fragmenting restriction endonuclease and said first restriction endonuclease are the same.

23. A method for detecting a first target nucleic acid present in a first nucleic acid population (a first nucleic acid sample) and not in a second nucleic acid population (a second nucleic acid sample), and a second target nucleic acid present in both said first nucleic acid sample and said second nucleic acid sample, said method comprising:

(a) separately fragmenting nucleic acid from said first nucleic acid sample and nucleic acid from said second nucleic acid sample with a sample fragmenting restriction endonuclease to create first nucleic acid sample fragments and second nucleic acid sample fragments, respectively;

(b) ligating a pair of first nucleic acid adaptors onto said first nucleic acid sample fragments, each adaptor having a first restriction endonuclease recognition site that is cleaved by a first restriction endonuclease, and amplifying said first nucleic acid sample fragments with a primer having a sequence that is complementary to a sequence of said first nucleic acid adaptors;

(c) ligating a pair of second nucleic acid adaptors onto said second nucleic acid sample fragments, each adaptor having a second restriction endonuclease recognition site which is cleaved by a second restriction endonuclease that recognizes all or a part of said first restriction endonuclease recognition site, but cleaves so that different ends are created between said first nucleic acid sample fragments and said second nucleic acid sample fragments, and amplifying said second nucleic acid sample fragments with a primer having a sequence that is complementary to a sequence of the second nucleic acid adaptors;

(d) fragmenting said first nucleic acid sample fragments with said first restriction endonuclease and said second nucleic acid sample fragments with said second restriction endonuclease; then (e) combining said first nucleic acid sample fragments and said second nucleic acid sample fragments under hybridization conditions to form a hybridization mixture;

(f) isolating a homoduplex from said hybridization mixture, wherein the isolation of said homoduplex identifies first target nucleic acid present in said first nucleic acid sample and not in said second nucleic acid sample; and (g) isolating a heteroduplex from said hybridization mixture, wherein the isolation of said heteroduplex identifies second target nucleic acid which is present in both said first nucleic acid sample and said second nucleic acid sample.

24. The method in accordance with claim 23, wherein said nucleic acid is cDNA.

25. The method in accordance with claim 23, wherein said nucleic acid is derived from a source selected from the group consisting of eukaryotic, prokaryotic, invertebrate, vertebrate, mammalian, non-mammalian and plant.

26. The method in accordance with claim 23, wherein said sample fragmenting restriction endonuclease and said first restriction endonuclease are the same.

27. The method in accordance with claim 23, wherein said sample fragmenting restriction endonuclease and said first restriction endonuclease are both HinpI, and said second restriction endonuclease is HhaI.

28. The method in accordance with claim 23, wherein said sample fragmenting restriction endonuclease and said second restriction endonuclease are both HinP1I, and said first restriction endonuclease is HhaI.

29. The method in accordance with claim 23, wherein said sample fragmenting restriction endonuclease is HaeIII, said first restriction endonuclease is KasI, and said second restriction endonuclease is EheI.

30. The method in accordance with claim 23, wherein said homoduplex of step (g) is isolated from said hybridization mixture using a biotinylated nucleotide.

31. The method in accordance with claim 23, wherein said homoduplex of step (g) is isolated from said hybridization mixture by ligating a pair of adaptors onto said homoduplex.

32. The method in accordance with claim 23, wherein said heteroduplex of step (h) is isolated from said hybridization mixture using a biotinylated nucleotide.

33. The method in accordance with claim 23, wherein said heteroduplex of step (h) is isolated from said hybridization mixture by ligating a pair of adaptors onto said homoduplex.

34. The method in accordance with claim 23, wherein said first restriction endonuclease and said second restriction endonuclease, respectively, are selected from the group consisting of:

HinP1I and HhaI;
HinP1I and CfoI;
Csp6I and RsaI;
HinP1I and BssHII;
MseI and PacI;
AciI and BsrBI;
AciI and SacII;
KasI and EheI;
Acc65I and KpnI;
ApaI and Bsp120I;
Ppu10I and NsiI; and
SmaI and XmaI.

35. The method in accordance with claim 34, wherein said sample fragmenting restriction endonuclease and said first restriction endonuclease are the same.

36. A method for detecting a target nucleic acid present in a first nucleic acid population (a first nucleic acid sample) and not in a second nucleic acid population (a second nucleic acid sample), said method comprising:

(a) fragmenting said first nucleic acid sample with a first restriction endonuclease to create first nucleic acid sample fragments and said second nucleic acid sample with a second restriction endonuclease to create second nucleic acid sample fragments, said second restriction endonuclease recognizing all or a part of said first restriction endonuclease recognition site, but cleaving so that different ends are created between said first nucleic acid sample fragments and said second nucleic acid sample fragments; then (b) combining said first nucleic acid sample fragments and said second nucleic acid sample fragments under hybridization conditions to form a hybridization mixture; and (c) isolating a homoduplex from said hybridization mixture, wherein the isolation of said homoduplex identifies target nucleic acid which is present in said first nucleic acid sample and not in said second nucleic acid sample.

37. The method in accordance with claim 36, wherein said nucleic acid is cDNA.

38. The method in accordance with claim 36, wherein said nucleic acid is derived from a source selected from the group consisting of eukaryotic, prokaryotic, invertebrate, vertebrate, mammalian, non-mammalian and plant.

39. The method in accordance with claim 36, wherein said first restriction endonuclease and said second restriction endonuclease, respectively, are selected from the group consisting of:

HinP1I and HhaI;
HinP1I and CfoI;
Csp6I and RsaI;
HinP1I and BssHII;
MseI and PacI;
AciI and BsrBI;
AciI and SacII;
KasI and EheI;
Acc65I and KpnI;
ApaI and Bsp120I;
Ppu10I and NsiI; and
SmaI and XmaI.

40. The method in accordance with claim 36, wherein said homoduplex of step (c) is isolated from said hybridization mixture using a biotinylated nucleotide.

41. The method in accordance with claim 36, wherein said homoduplex of step (c) is isolated from said hybridization mixture by ligating a pair of adaptors onto said homoduplex.

42. A method for detecting a target nucleic acid present in both a first nucleic acid population (a first nucleic acid sample) and a second nucleic acid population (a second nucleic acid sample), said method comprising:

(a) fragmenting said first nucleic acid sample with a first restriction endonuclease to creat first nucleic acid sample fragments and said second nucleic acid sample fragments with a second restriction endonuclease to create second nucleic acid sample fragments, said second restriction endonuclease recognizing all or a part of said first restriction endonuclease recognition site, but cleaving so that different ends are created between said first nucleic acid sample fragments and said second nucleic acid sample fragments; then (b) combining said first nucleic acid sample fragments and said second nucleic acid sample fragments under hybridization conditions to form a hybridization mixture; and (c) isolating a heteroduplex from said hybridization mixture, wherein the isolation of said heteroduplex identifies second target nucleic acid which is present in both said first nucleic acid sample and said second nucleic acid sample.

43. The method in accordance with claim 42, wherein said nucleic acid is cDNA.

44. The method in accordance with claim 42, wherein said nucleic acid is derived from a source selected from the group consisting of eukaryotic, prokaryotic, invertebrate, vertebrate, mammalian, non-mammalian and plant.

45. The method in accordance with claim 42, wherein said first restriction endonuclease and said second restriction endonuclease, respectively, are selected from the group consisting of:

HinP1I and HhaI;
HinP1I and CfoI;
Csp6I and RsaI;
HinP1I and BssHII;
MseI and PacI;
AciI and BsrBI;
AciI and SacII;
KasI and EheI;
Acc65I and KpnI;
ApaI and Bsp120I;
Ppu10I and NsiI; and
SmaI and XmaI.

46. The method in accordance with claim 42, wherein said heteroduplex of step (c) is isolated from said hybridization mixture using a biotinylated nucleotide.

47. The method in accordance with claim 42, wherein said heteroduplex of step (c) is isolated from said hybridization mixture by ligating a pair of adaptors onto said heteroduplex.

48. A method for detecting a first target nucleic acid present in a first nucleic acid population (a first nucleic acid sample) and not in a second nucleic acid population (a second nucleic acid sample), and a second target nucleic acid present in both said first nucleic acid sample and said second nucleic acid sample, said method comprising:

(a) fragmenting said first nucleic acid sample with a first restriction endonuclease to creat first nucleic acid sample fragments and said second nucleic acid sample fragments with a second restriction endonuclease to create second nucleic acid sample fragments, said second restriction endonuclease recognizing all or a part of said first restriction endonuclease recognition site, but cleaving so that different ends are created between said first nucleic acid sample fragments and said second nucleic acid sample fragments; then (b) combining said first nucleic acid sample fragments and said second nucleic acid sample fragments under hybridization conditions to form a hybridization mixture;

(c) isolating a homoduplex from said hybridization mixture, wherein the isolation of said homoduplex identifies first target nucleic acid present in said first nucleic acid sample and not in said second nucleic acid sample; and (d) isolating a heteroduplex from said hybridization mixture, wherein the isolation of said heteroduplex identifies second target nucleic acid which is present in both said first nucleic acid sample and said second nucleic acid sample.

49. The method in accordance with claim 48, wherein said nucleic acid is cDNA.

50. The method in accordance with claim 48, wherein said nucleic acid is derived from a source selected from the group consisting of eukaryotic, prokaryotic, invertebrate, vertebrate, mammalian, non-mammalian and plant.

51. The method in accordance with claim 48, wherein said first restriction endonuclease and said second restriction endonuclease, respectively, are selected from the group consisting of:

HinP1I and HhaI;
HinP1I and CfoI;
Csp6I and RsaI;
HinP1I and BssHII;
MseI and PacI;
AciI and BsrBI;
AciI and SacII;
KasI and EheI;
Acc65I and KpnI;
ApaI and Bsp120I;
Ppu10I and NsiI; and
SmaI and XmaI.

52. The method in accordance with claim 48, wherein said homoduplex of step (c) is isolated from said hybridization mixture using a biotinylated nucleotide.

53. The method in accordance with claim 48, wherein said homoduplex of step (c) is isolated from said hybridization mixture by ligating a pair of adaptors onto said homoduplex.

54. The method in accordance with claim 48, wherein said heteroduplex of step (d) is isolated from said hybridization mixture using a biotinylated nucleotide.

55. The method in accordance with claim 48, wherein said heteroduplex of step (d) is isolated from said hybridization mixture by ligating a pair of adaptors onto said homoduplex.

* * * * *